United States Patent [19]

Iga et al.

[11] Patent Number: 4,730,932
[45] Date of Patent: Mar. 15, 1988

[54] TRANSMISSIVITY INSPECTION APPARATUS

[75] Inventors: Masahiko Iga, Saitama; Yoshihiro Yamato, Yokohama; Yoshio Yamaguchi, Hiratsuka, all of Japan

[73] Assignees: Kabushiki Kaisha Toshiba, Kawasaki; Toyo Glass Co., Ltd., Tokyo, both of Japan

[21] Appl. No.: 9,752

[22] Filed: Feb. 2, 1987

[30] Foreign Application Priority Data

Jan. 31, 1986 [JP] Japan ................................. 61-19615

[51] Int. Cl.⁴ ........................................... G01N 21/17
[52] U.S. Cl. ................................... 356/432; 356/446
[58] Field of Search ............... 356/432, 433, 440, 443, 356/444, 382

[56] References Cited

U.S. PATENT DOCUMENTS

| | | | |
|---|---|---|---|
| 3,680,965 | 8/1972 | Dilworth et al. | 356/213 |
| 3,693,025 | 9/1972 | Brunton | 356/382 |
| 3,807,870 | 4/1974 | Kalman | 356/382 |

FOREIGN PATENT DOCUMENTS 48-13476  4/1973  Japan .
48-10432  4/1973  Japan .

*Primary Examiner*—R. A. Rosenberger
*Attorney, Agent, or Firm*—Oblon, Fisher, Spivak, McClelland & Maier

[57] ABSTRACT

In a transmissivity inspection apparatus, laser beam is radiated onto an object to be inspected. Irregularly reflected laser light components produced from the object are detected by a photoelectric converter element. The transmissivity of the object with respect to the laser beam is inspected by a discriminator, based on a specific pattern of the irregularly reflected laser light components detected by the photoelectric converter element. The specific pattern of a transparent substance differs from that of a nontransparent substance, thereby to discriminate the nontransparent substance from the transparent substance.

11 Claims, 54 Drawing Figures

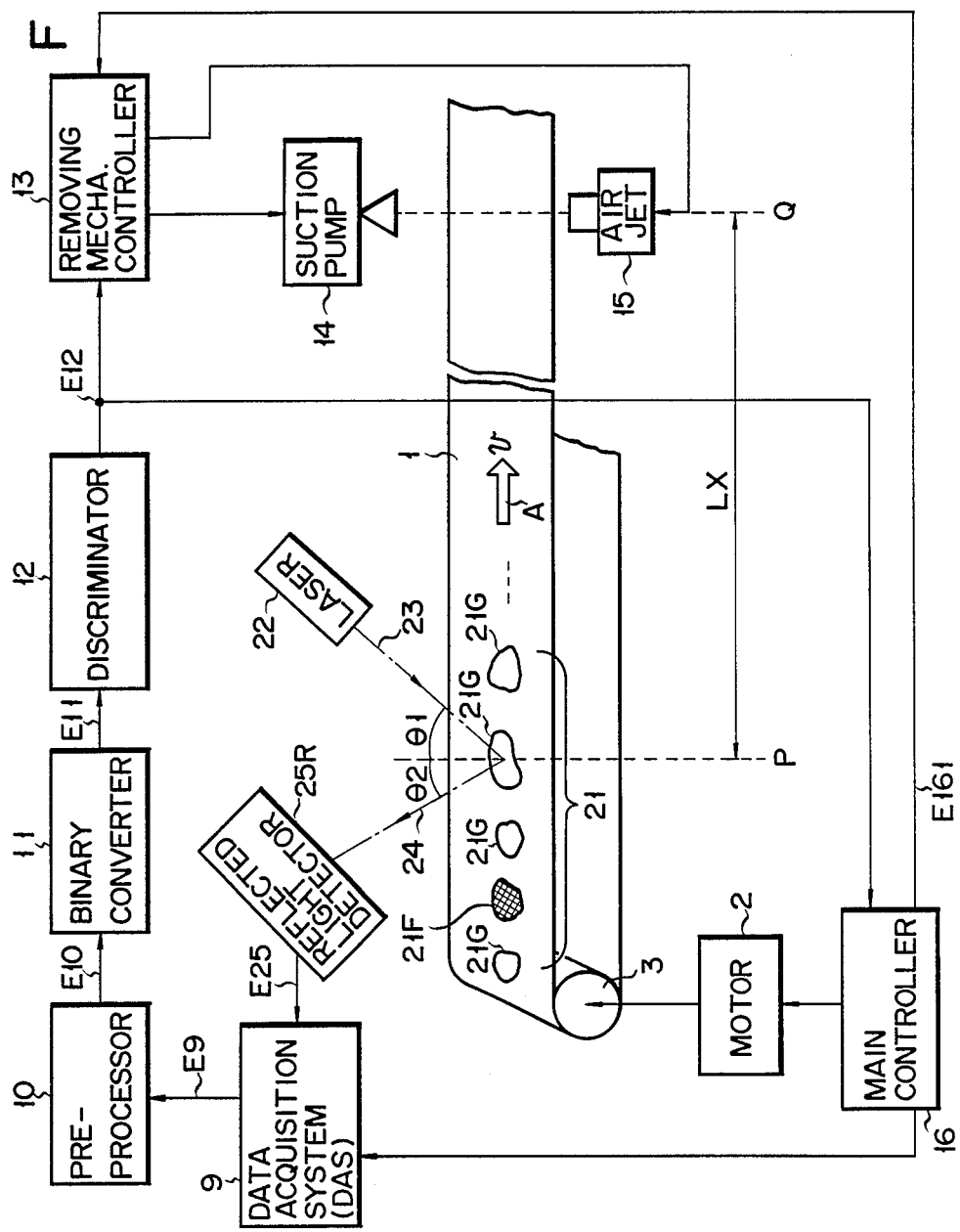

FIG. 8
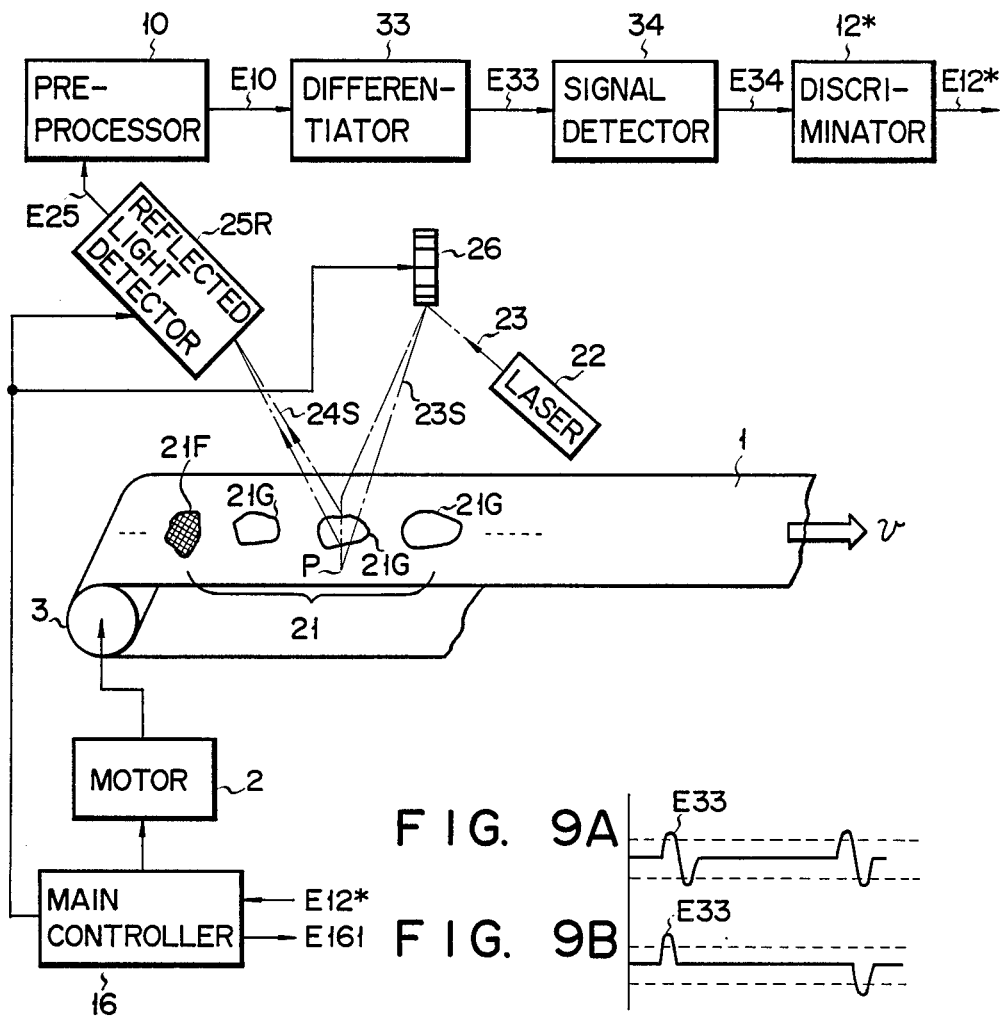
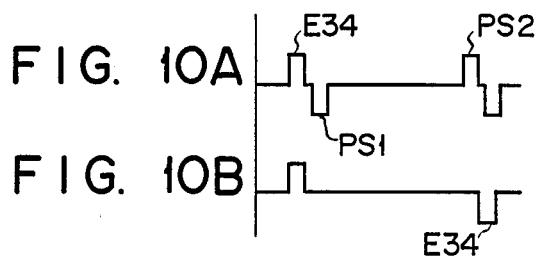
FIG. 9A
FIG. 9B
FIG. 10A
FIG. 10B

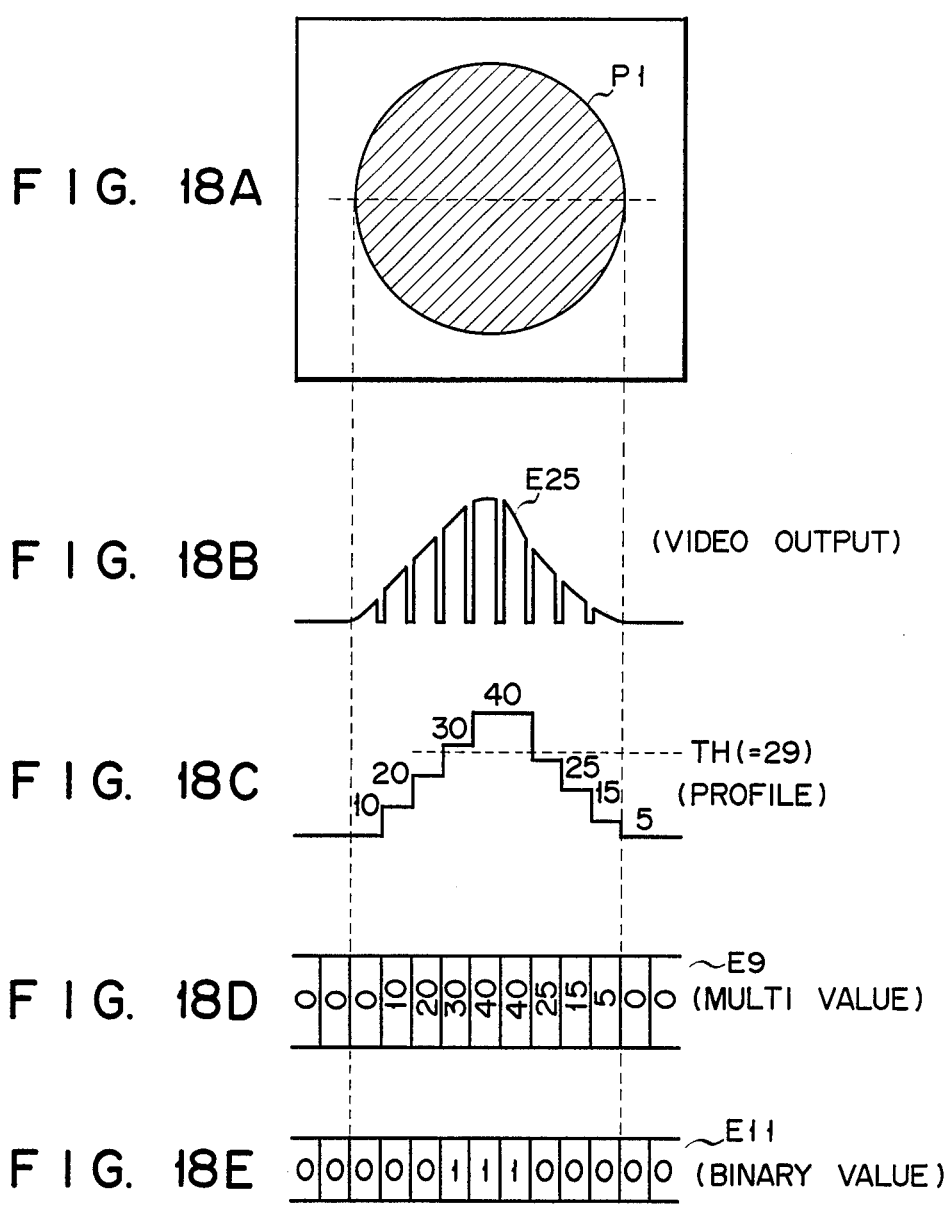

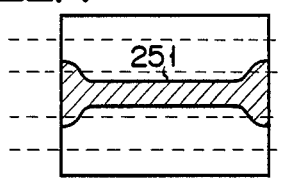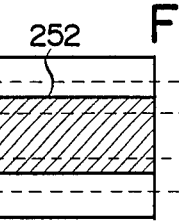
FIG. 22A  FIG. 23A
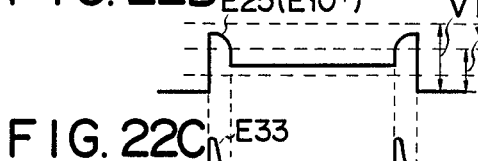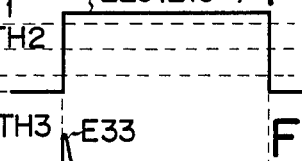
FIG. 22B  FIG. 23B
FIG. 22C  FIG. 23C
FIG. 22D  FIG. 23D
FIG. 22E  FIG. 23E
FIG. 23F
FIG. 22F
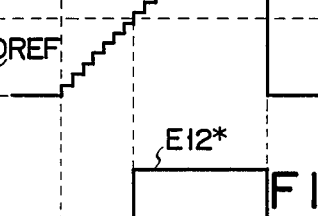
FIG. 22G  FIG. 23G
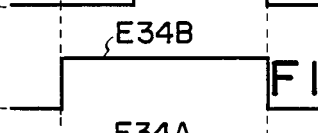
FIG. 22H  FIG. 23H
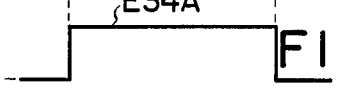
FIG. 22I  FIG. 23I

TRANSMISSIVITY INSPECTION APPARATUS

BACKGROUND OF THE INVENTION

The present invention relates to a transmissivity inspection apparatus which is applied to a glass molding technique and is used for detecting and removing nontransparent substances for coherent light, such as stones, ceramics, and the like, mixed in transparent substances for coherent light, such as glass fragments.

In general, glass molding includes a process of charging transparent glass fragments as raw materials into a furnace to melt them. In this process, if nontranslucent or nontransparent foreign matter other than the glass fragments, such as stones, ceramics, and the like are mixed in the glass fragments, defective products are molded, and the furnace itself could be damaged. Therefore, it is important to remove foreign matter from recovered glass fragments during the glass molding processes.

Since there is no apparatus for automatically detecting foreign matter from glass fragments, the foreign matter removing operation must be done by observation of human inspectors. For this reason, they sometimes fail to detect foreign matter due to eye fatigue or carelessness, and it is difficult to reliably remove foreign matter. Such a manual operation slows the line operation rate, and also poses problems in view of automation and labor costs.

SUMMARY OF THE INVENTION

It is accordingly an object of the present invention to provide a transmissivity inspection apparatus which can automatically and reliably detect nontranslucent or nontransparent substances mixed in translucent or transparent substances.

To achieve the above object of the present invention, coherent light is radiated onto an object to be inspected, irregularly reflected light components produced in the object are detected, and a transmissivity of the object with respect to the light is inspected based on the irregularly reflected light components detected.

BRIEF DESCRIPTION OF THE DRAWINGS

FIGS. 1 to 6A and 6B explain the principle of the operation of this invention, in which:

FIG. 1 is a view showing states of reflection, absorption, and transmission of light (laser beam), FIG. 2 is a view showing a mechanism of the reflected light detection, FIGS. 3A to 3E respectively illustrate reflection patterns of glass and foreign matter upon radiation of laser beam spots, FIG. 5 is a view showing a mechanism for scanning laser beams, and FIGS. 6A and 6B respectively illustrate reflection patterns of the glass and foreign matter upon scanning of the laser beam;

FIG. 7 is a block diagram showing the arrangement of a first embodiment of the present invention;

FIGS. 8 to 10 show a second embodiment of the present invention, in which:

FIG. 8 is a block diagram showing the main part of the second embodiment, and

FIGS. 9A and 9B show signal waveforms input to the signal detector in FIG. 8;

FIGS. 10A and 10B show signal waveforms output from the signal detector in FIG. 8;

FIGS. 11 to 13 show a third embodiment of the present invention, in which:

FIG. 11 is a block diagram showing the main part of the third embodiment,

FIG. 12 illustrates an example of the location of irradiation beam positions (N1, N2), and FIG. 13 is a flow chart for explaining the function of the discriminator in FIG. 11;

FIG. 7);

FIG. 7);

FIGS. 18A–18E exemplify the contents of signals obtained from the circuit elements in FIG. 17.

FIGS. 22A–22I are timing charts explaining how a translucent pattern (251) is discriminated by the discriminator (12*) in FIG. 8;

FIGS. 23A–23I are timing charts explaining how a nontranslucent pattern (252) is discriminated by the discriminator (12*) in FIG. 8;

DETAILED DESCRIPTION OF THE PREFERRED EMBODIMENTS

Figure 1:
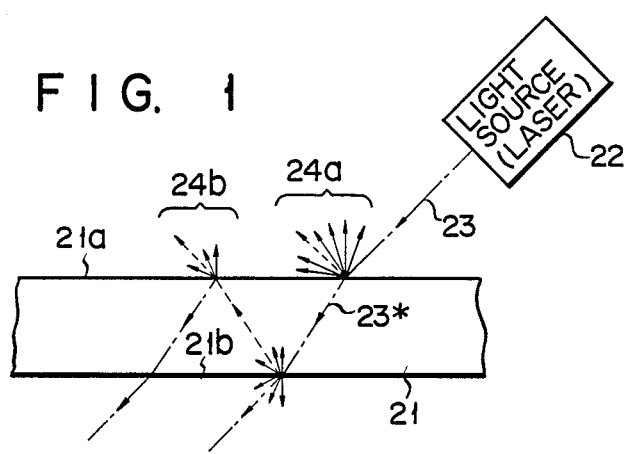

Hereinafter, preferred embodiments of the invention will be described in detail with reference to the accompanying drawings. In the following description, the same or similar elements are denoted by the same or similar reference numerals throughout the drawings, thereby avoiding redundant explanations.

The principle of the present invention will be described first. As shown in FIG. 1, laser beam 23 is radiated from light (laser) source 22 onto a substance (object 21 to be inspected), such as glass, which is transparent for coherent light. (Such a substance will be referred to as a translucent substance hereinafter). Then, laser beam 23 is scattered at surface 21a of the translucent substance due to its reflection, absorption, transmission, etc. Transmission beam 23* arrives at interface 21b while being absorbed during transmission to decrease in amount of light, and is also scattered at interface 21b due to its reflection, absorption, transmission, and the like. The same phenomenon is repeated at surface 21a or interface 21b.

Emission directions of reflected beams 24a and 24b depend on the surface condition of the translucent substance (21). More specifically, if the surface is almost a smooth plane, the amount of irregular reflection components (indicated by solid arrows in FIG. 1) decreases while the amount of regular reflection components (indicated by broken arrows in FIG. 1) increases.

When object 21 is a nontranslucent substance, such as stones, ceramics, and the like, an interference phenomenon including only reflection and absorption occurs on the surface of object 21, and there are no transmission beams.

Figure 2:
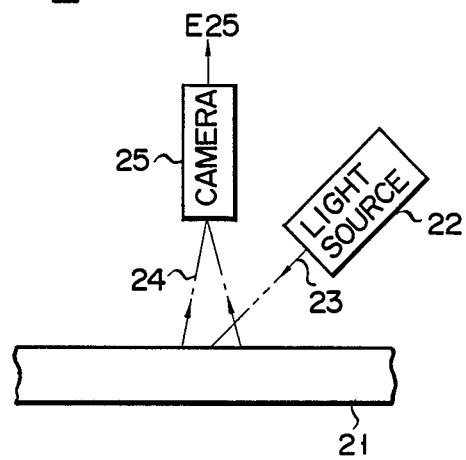

As objects 21, pieces of glass having different transmissivities and nontranslucent substances are selected, and are irradiated with laser beams 23 so as to detect irregular reflection components by camera 25, as shown in FIG. 2.

Figure 3:
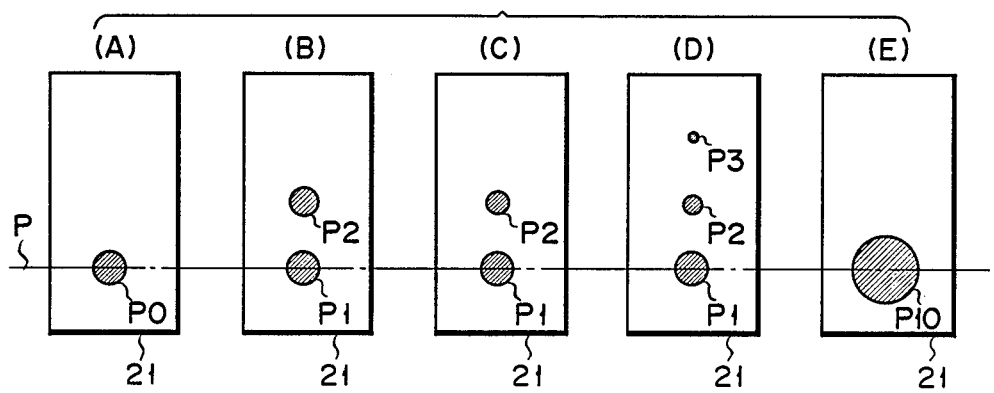

FIGS. 3A-3E exemplifies several reflection patterns (slanted portions) scanned by camera 25. FIG. 3A shows an irradiation pattern of light source 22 (irradiation position or beam spot position is indicated by P); FIG. 3B shows a reflection pattern of a piece of glass with low transmissivity; FIG. 3C shows a reflection pattern of a piece of glass with medium transmissivity; FIG. 3D shows a reflection pattern of a piece of glass with high transmissivity; and FIG. 3E shows a reflection pattern of a nontranslucent substance.

As will be seen from the illustration of FIGS. 3A–3E, irregular reflection patterns (slanted portions) of pieces of glass (translucent substances) and nontranslucent substances are largely different from each other. More specifically, in the case of glass (FIGS. 3B to 3D), primary reflection pattern P1 is substantially the same as irradiation pattern P0 of light source 22 (FIG. 3A), and secondary and tertiary reflections (patterns P2 and P3) occur. In contrast to this, in the case of the nontranslucent substances (FIG. 3E), the area of primary reflection pattern P10 becomes larger than that of irradiation pattern P0 of light source 22, and secondary and tertiary reflections (patterns P2 and P3) do not occur.

Figure 4A:
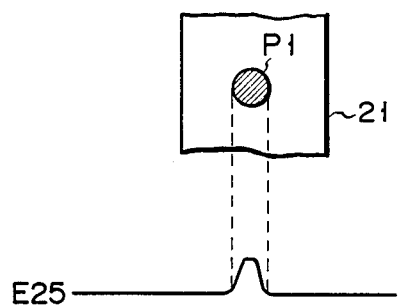
FIGS. 4A and 4B show waveforms of electrical signals corresponding to the reflection patterns of the glass and foreign matter.
Figure 4B:
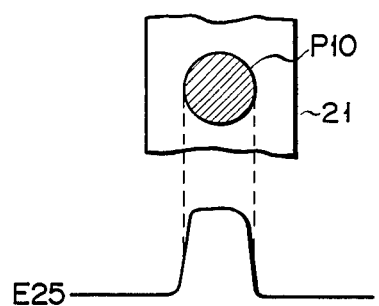

In the arrangement of FIG. 2, assume that a photoelectric converter is used in place of camera 25 to detect reflected beams 24. Then, electrical signal E25, output from the photoelectric converter, has a waveform as shown in FIG. 4A, if object 21 is glass whose transmissivity is equal to or higher than a predetermined transmissivity, and has a waveform as shown in FIG. 4B, if object 21 is a nontranslucent substance whose transmissivity is lower than the predetermined transmissivity. As can be seen from FIGS. 4A and 4B, the signal level or amplitude of signal E25 obtained for glass (translucent substance) greatly differs from that obtained for a nontranslucent substance.

Figure 5:
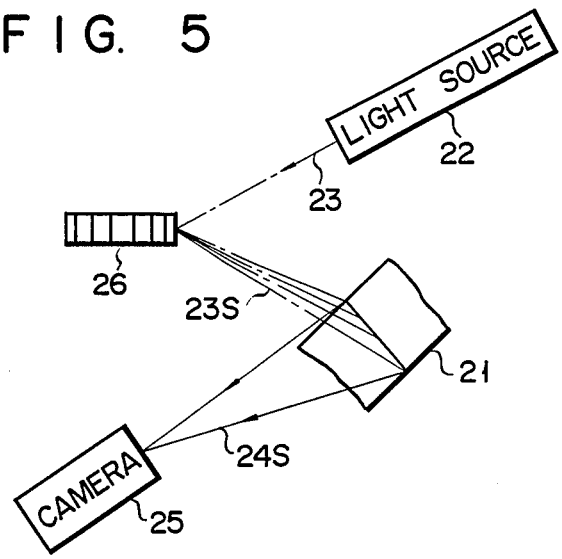

In the arrangement of FIG. 5, laser beam 23 is converted into scan beam 23S by scanning the direction of beam 23 in the widthwise direction of object 21 using rotary mirror 26, and scan beam 23S is radiated onto object 21. Then, reflection pattern P25 (FIGS. 6A and 6B), formed by the scanning of beam 23S, is detected by camera 25.

Figure 6A:
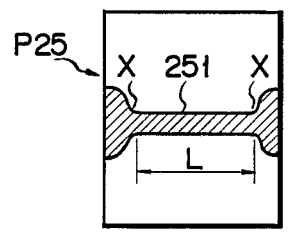

When object 21 is glass having a transmissivity higher than a predetermined transmissivity, it causes a pattern with different widths because the intensity of scanned reflected beams 24S obtained at each of two end portions of object 21 is larger than that obtained at the intermediate portion thereof, as shown by the slanted portion 251 in FIG. 6A. When object 21 is a nontranslucent substance having a transmissivity lower than the predetermined transmissivity, it causes a pattern with a substantially constant width, as shown by the slanted portion 252 in FIG. 6B. Therefore, by detecting abrupt changes (X in FIG. 6A) in reflection pattern P25 or detecting a certain length (L in FIG. 6A) of the narrowed portion of reflection pattern P25, glass can be distinguished from a nontranslucent substance.

More specifically, when reflection pattern P25 (FIG. 6A) has portion X indicating abrupt change, or when pattern P25 includes narrowed portion 251 with length L, it can be discriminated as glass. On the other hand, when reflection pattern P25 (FIG. 6B) does not have a portion indicating abrupt change, it can be discriminated as a nontranslucent substance.

The present invention has been made on the basis of the aforementioned principle, and embodiments of the present invention will now be described with reference to the accompanying drawings.

FIG. 7 is a block diagram showing a system configuration of a first embodiment of the present invention. In FIG. 7, reference numeral 1 denotes a conveyor belt line (to be referred to simply as a conveyor line hereinafter). Conveyor line 1 is pivoted upon rotation of roller 3, and roller 3 is driven by motor 2, so that objects 21 to be inspected are fed, one by one, to the next process (in the direction indicated by arrow v). Usually, objects 21, mixed with foreign matter (stones, ceramics, etc.) 21F, are glass fragments 21G used in a glass molding process.

Light source 22 emits coherent light, for example, laser beam 23. Laser beam 23 is sequentially radiated onto point P, as shown in FIG. 7, to form a beam spot on object 21. Reflected light detector 25R, formed of a plurality of photoelectric converters, detects from reflected beam 24 the irregular reflection components of laser beam 23. Thus, when object 21 is a plate-like fragment, detector 25R detects the patterns as shown in FIGS. 4A and 4B. More specifically, the photoelectric converters of detector 25R are arranged at given positions at which reflected beam 24 with reflection angle $\theta 2$ which is different from laser beam incident angle $\theta 1$, can be detected.

Data acquisition system (DAS) 9 acquires electrical signals E25 from the respective photoelectric converters of detector 25R, and acquired signals E9 are subjected to predetermined preprocessing, such as filtering, in preprocessor 10. Thereafter, preprocessed signal E10 from preprocessor 10 is converted to binary signal E11 via binary converter 11. This binary signal E11 represents a signal obtained by level-slicing signal E25 shown in FIGS. 4A and 4B.

Discriminator 12 discriminates, based on binary signal E11 delivered from converter 11, whether object 21 is glass fragment 21G or foreign matter 21F. If it is discriminated that object 21 under inspection is foreign matter 21F, foreign matter removal instruction (inspection signal) E12 is supplied to removing mechanism controller 13. Here, a material, having a transmissivity lower than a predetermined transmissivity, is defined as foreign matter 21F. Removing mechanism controller 13 controls driving operations of suction pump 14 and air jet 15 arranged opposite thereto. Upon operation of suction pump 14 and air jet 15, only foreign matters 21F contained in many objects 21 are removed from conveyor line 1.

Main controller 16 controls start timing and rotating speed of motor 2, and also controls data acquisition timing of DAS 9 as well as activation timing of removing mechanism controller 13. The activation timing of controller 13 is determined by removal start instruction E161 generated from controller 16. The generation timing of instruction E161 depends on feeding speed v of conveyor line 1, distance LX between beam spot position P and foreign matter removing position Q, and the timing of generation of instruction E12.

The operation of the first embodiment in FIG. 7 will now be described.

Motor (pulse motor) 2 is driven under the control of main controller 16, and conveyor line 1 runs so that objects 21 are conveyed, one by one, along line 1. In this state, laser beam 23 is radiated from light source 22 onto object 21 to form a laser spot thereon. Then, irregular reflection components of beam 24, reflected by the surface of object 21, are detected by reflected light detector 25R. Detector 25R converts the reflection components of beam 24 to electrical signal E25, and signal E25 is then acquired by DAS 9.

When object 21 is glass fragment 21G, the signal level of E25 acquired by DAS 9 is low, as shown in FIG. 4A. When object 21 is foreign matter 21F, the signal level of E25 is high as shown in FIG. 4B.

Electrical signal E25 is subjected to predetermined preprocessing in preprocessor 10, and is then converted into binary signal E11 via binary converter 11, using a threshold level being higher than the signal level of E25 obtained for glass fragment 21G but lower than that obtained for foreign matter 21F.

When the level of signal E25 is lower than the above-mentioned threshold level, all binary signals E11 corresponding to E25 are "0". However, if signal E25 includes portions having signal levels higher than said threshold level, signals of "1" are contained in binary signals E11. Discriminator 12 receives such binary signals (E11) delivered from binary converter 11. When signal E11 includes "1", discriminator 12 discriminates that object 21 presently inspected includes foreign matter 21F, and it outputs foreign matter removal instruction E12 to removing mechanism controller 13 as well as to main controller 16.

Removing mechanism controller 13 is controlled by main controller 16 in accordance with the relationship between distance LX between the beam spot position P of laser beam 23 and position Q of pump 14 and air jet 15, and with the feeding speed of conveyor line 1. If controller 13 receives removal instruction E12 from discriminator 12, it activates pump 14 and air jet 15 when removal start instruction E161 is supplied from main controller 16. Then, at position Q, foreign matter 21F is blown by air jet 15, and is drawn by suction pump 14. In this manner, foreign matter 21F is removed from conveyor line 1.

According to the first embodiment in FIG. 7, laser beam 23 is radiated onto object 21, which is conveyed along conveyor line 1, to form beam spots thereon, and irregular reflection components of reflected beams 24 upon laser beam radiation are detected and converted to electrical signal E25. It is then discriminated by discriminator 12, based on the signal levels of electrical signal E25, whether object 21 under inspection is glass fragment 21G or foreign matter 21F. If object 21 is discriminated to be foreign matter 21F, foreign matter 21F is removed from line 1 by the action of pump 14 and air jet 15.

As shown in FIGS. 4A and 4B, signal levels of glass fragment 21G and foreign matter 21F are considerably different from each other. Therefore, when electrical signal E25 is converted into binary signals using a predetermined threshold value, glass fragment 21G and foreign matter 21F can be distinguished from each other with high reliability.

When the apparatus of the present invention is applied to a foreign matter removing apparatus in the glass manufacturing process, removal of foreign matter 21F can be automatically and reliably performed, thus improving a line operation rate and achieving automation.

Another embodiment of the present invention will now be described.

FIG. 8 is a block diagram showing the main part of a second embodiment of the present invention. In this embodiment, laser beam 23 emitted from light source 22 is converted into linearly scanned beam 23S by rotary mirror 26, and scanned beam 23S is radiated onto object 21 along the widthwise direction of conveyor line 1. Namely, beam 23S is scanned along line P. The reflection pattern of each of objects 21 is detected by reflected light detector 25R which is formed of a line sensor.

Figure 6B:
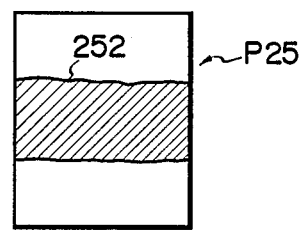

When object 21 is glass fragment 21G, the reflection pattern, detected by detector 25R, becomes a specific pattern whose two ends indicate irregular reflection and which has a narrow intermediate portion, as shown in FIG. 6A. However, when object 21 is foreign matter 21F, the entire detected pattern indicates significant irregular reflection, as shown in FIG. 6B.

The reflection pattern is subjected to predetermined preprocessing by preprocessor 10. Preprocessed output E10 from preprocessor 10 is differentiated by differentiator 33 to detect the rate of change of the signal edge of output E10. The waveform of differentiated output signal E33 from differentiator 33 is shown in FIG. 9A when object 21 is glass fragment 21G, and is shown in FIG. 9B when it is foreign matter 21F.

Signal E33 is converted into pulse signal E34, via signal detector 34, using predetermined positive and negative threshold levels. By the operation of signal detector 34, differentiated signal E33 of FIG. 9A is converted into pulse signal E34 of FIG. 10A, and differentiated signal E33 of FIG. 9B is converted into pulse signal E34 of FIG. 10B. Pulse signal E34 shown in FIG. 10A is detected in the case of glass fragment 21G, and pulse signal E34 shown in FIG. 10B is detected in the case of the foreign matter 21F.

If pulse signal E34 includes portions PS1 and PS2 as shown in FIG. 10A, foreign matter discriminator 12* discriminates glass fragment 21G having a transmissivity higher than a predetermined transmissivity. If pulse signal E34 does not include portions PS1 and PS2 as shown in FIG. 10B, foreign matter discriminator 12* discriminates foreign matter 21F having a transmissivity lower than the predetermined transmissivity, and generates foreign matter removal instruction E12*. When a removing mechanism similar to that in the first embodiment is used, foreign matter 21F can be removed in accordance with the generation of removal instruction E12*.

In this manner, when scanned laser beam 23S is radiated on object 21, a reflection pattern, obtained from each object 21, is detected to obtain a rate of change of this reflection pattern, to thereby detect foreign matter 21F. Note that in the embodiment of FIG. 8, laser beam 23S is scanned in the widthwise direction of object 21. However, if the beam spot of laser beam 23S can always be radiated on the end portion of object 21, even if laser beam 23 is not scanned, the rate of change of the reflection pattern can be simply obtained to detect foreign matter 21F.

Figure 11:
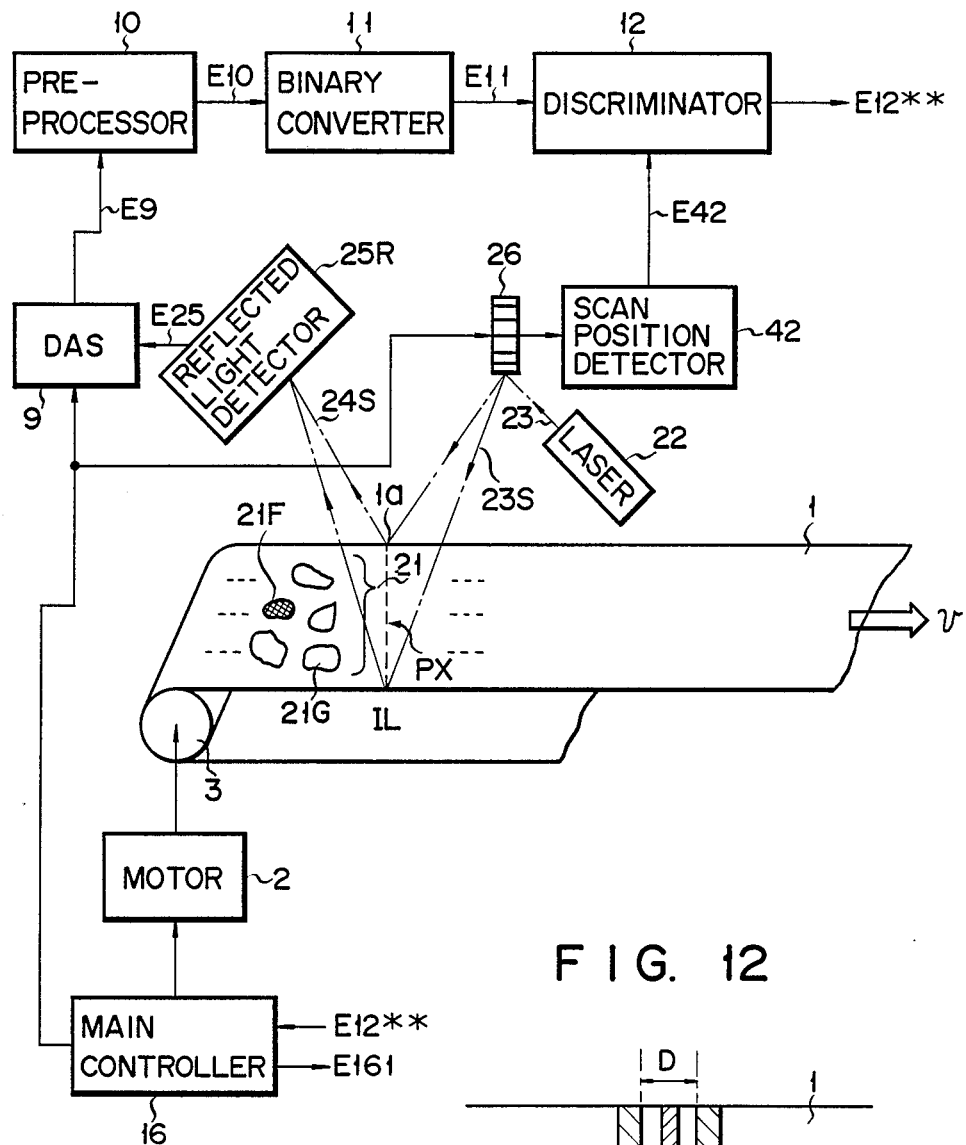

FIG. 11 is a block diagram showing the main part of a third embodiment of the present invention. In the first and second embodiments, the case has been exemplified wherein objects 21 are conveyed along conveyor line 1 one by one. In the embodiment of FIG. 11, however, a plurality of objects 21 are irregularly conveyed, and laser beam 23S, obtained via rotary mirror 26 from light source 22, is scanned in the widthwise direction of conveyor line 1. Then, reflected beams (irregular reflection components) 24S from objects 21 are detected for each scanning operation by reflected light detector 25R on which a plurality of photoelectric conversion elements (not shown) are aligned.

Figure 12:
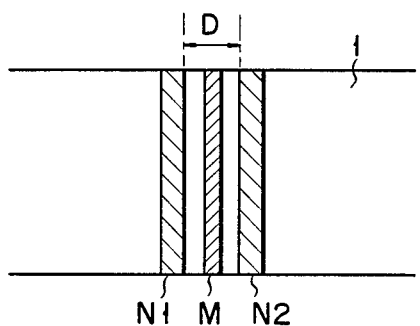

Detector 25R receives, at its photoelectric conversion elements, reflected beams 24S from positions N1 and N2 of conveyor line 1, which are separated by distance D (see FIG. 12). Laser beam irradiation position M on conveyor line 1 is located at the center of distance D, as shown in FIG. 12.

Distance D is larger than the width of the narrowed portion of reflection pattern 251 (FIG. 6A) of glass fragment 21G, but is smaller than the width of reflection pattern 252 (FIG. 6B) of foreign matter 21F.

In this manner, electrical signal E25 output from detector 25R is converted into binary signal E11 via circuit elements 9 to 11. When object 21 is glass fragment 21G, binary signals E11 with "0" are continued, but binary signal E11 with "1" is generated at a position corresponding to the end portion of object 21. On the other hand, when object 21 is foreign matter 21F, signals E11 with "1" are continued.

Discriminator 12 performs foreign matter discrimination based on binary signals E11. Discriminator 12 also detects specific conveyance position PX of foreign matter 21F in accordance with scan position signal E42 detected by scan position detector 42, which indicates the position of scanning of beam 23S with respect to irradiation locus IL along the widthwise direction of on conveyor line 1. To be specific, discriminator 12 may include a rotary encoder (not shown), coupled to rotary mirror 26, for generating pulses indicating the scanning angle of beam 23S, and a microcomputer responsive to the pulses from the rotary encoder and binary signals E11 from binary converter 11.

Figure 13:
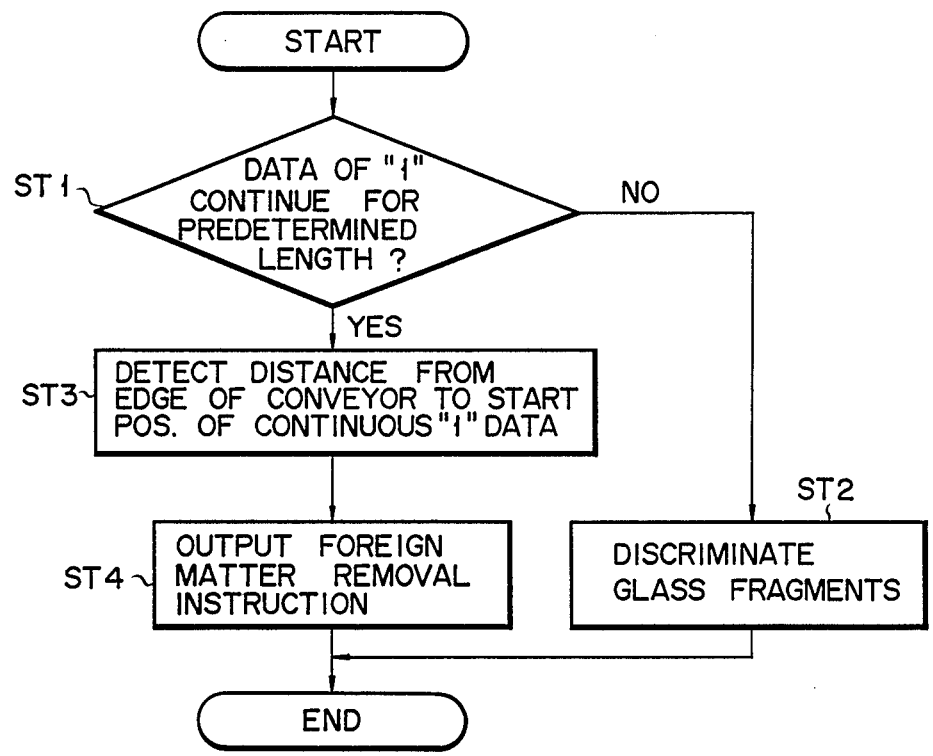

More specifically, discriminator 12 operates in accordance with the flow chart shown in FIG. 13. When binary signals E11 are received from binary converter 11, discriminator 12 checks whether or not the number of binary data "1" continues for a predetermined length (step ST1). If data "1" does not continue for the predetermined length, it is discriminated that no foreign matter 21F is present at the scan position of laser beam 23S, and that all objects 21 are glass fragments 21G (step ST2). However, if data "1" continues for the predetermined length, a distance, from the laser beam scan start position (e.g., side edge portion 1a of conveyor line 1) to the position from which the first one of the continuous data "1", is detected from laser beam scan position signal E42 (step ST3). Then, foreign matter removal instruction E12**, containing the widthwise distance information of step ST3, is sent to removing mechanism controller 13 of, e.g., FIG. 7 (step ST4).

Foreign matter 21F at specific conveyance position PX on line 1 can thus be removed upon operation of, for example, parallel-arranged plural sets of a pump (14) and air jet (15), one of which sets (14+15) is selectively activated in accordance with the widthwise distance information contained in removal instruction E12. Or, in place of the use of such parallel pump/air-jet sets, one parallel-slidable set of pump (14) and air jet (15), which can be moved along the widthwise direction of line 1 in accordance with the widthwise distance information of E12, can be used.

In this manner, even if objects 21 are irregularly conveyed along conveyor line 1, glass fragment 21G and foreign matter 21F can be automatically and reliably separated from each other.

A fourth embodiment of the present invention will now be described. The circuit configuration of this embodiment (not shown) may be the same as that shown in FIG. 7. As shown in FIGS. 3B-3E, sizes of reflection patterns (P1, P10), obtained by glass fragment 21G and foreign matter 21F with respect to laser beam spot P0, are different from each other. The fourth embodiment utilizes this difference of the reflection patterns.

Figure 14:
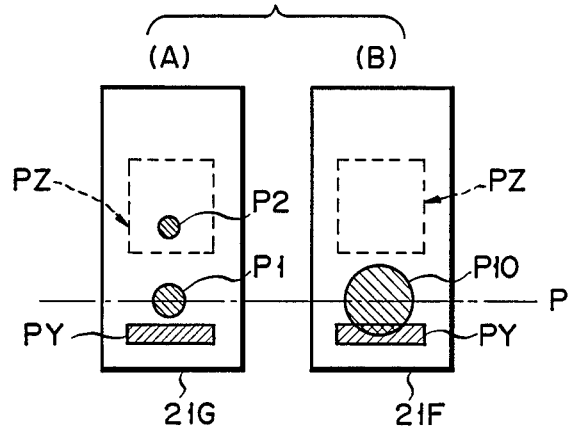
FIGS. 14A and 14B respectively illustrate reflection patterns of glass and foreign matter and photoelectric sensing areas near the irradiation position of laser beam spots, which are used for explaining a fourth embodiment of the present invention.

Thus, as will be seen from the illustration of FIGS. 14A and 14B, the fourth embodiment is provided with a photoelectric conversion element (not shown) responsive to reflection sensing area PY near irradiation position P, which is capable of detecting only reflection pattern P10 of foreign matter 21F whose transmissivity is lower than a predetermined transmissivity, without detecting reflection pattern P1 of glass fragment 21G. Such a photoelectric conversion element is arranged in place of reflected light detector 25R shown in FIG. 7 etc. In this manner, glass fragment 21G and foreign matter 21F can be distinguished from each other based on the output signal from the photoelectric conversion element.

In the fourth embodiment, only one photoelectric conversion element is satisfactory, to thereby provide an economical advantage.

Incidentally, a two-dimensional area sensor (not shown) for detecting reflection sensing area PZ in FIGS. 14A and 14B can be used in place of, or together with, the photoelectric conversion element for detecting reflection sensing area PZ. This two-dimensional area sensor is arranged such that it does not respond to foreign matter pattern P10 as shown in FIG. 3E, but it senses glass fragment patterns P2 and/or P3 as shown in FIGS. 3B-3D.

Figure 15:
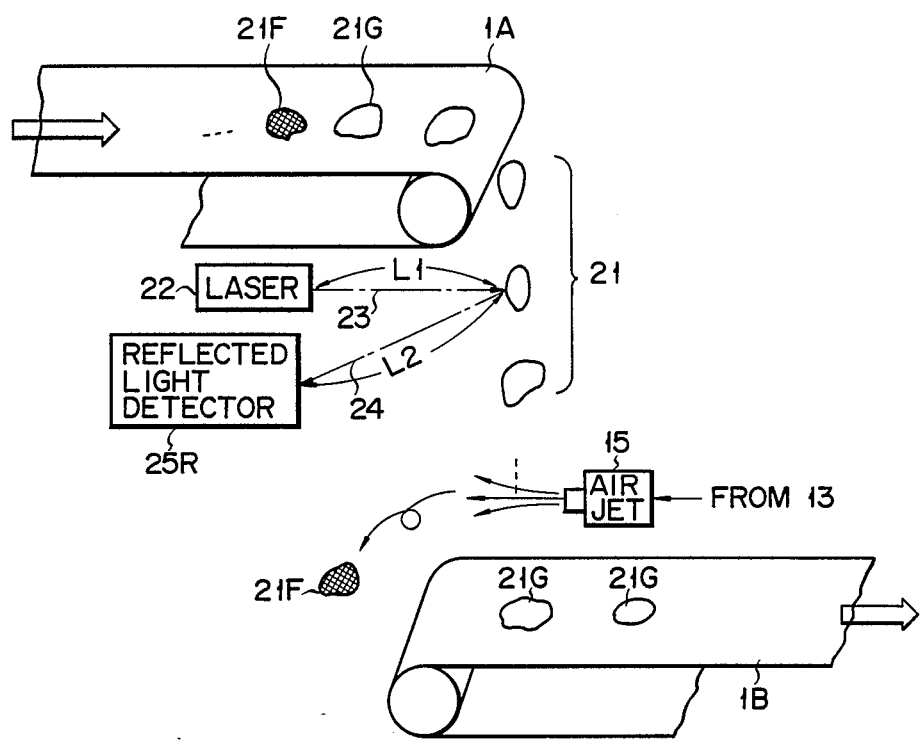
FIG. 15 is a block diagram showing the main part of a fifth embodiment of the present invention.

FIG. 15 is a block diagram showing the main part of a fifth embodiment of the present invention. The apparatus of this embodiment has the same functions as that of the first embodiment in FIG. 7. However, in this embodiment, inspection is performed not for objects 21 being conveyed along conveyor line 1, but for objects 21 falling from first conveyor line 1A to second conveyor line 1B, by irradiating them with laser beam 23.

In the fifth embodiment, reflected light detector 25R is coupled to circuit elements 9–12 of FIG. 7, so that the irregular reflection components of reflected beam 24 are discrimination, and glass fragments 21G and foreign matter 21F are distinguished from each other. During the falling process of foreign matter 21F, the detected foreign matter (21F) is blown by air jet 15, so that it does not fall on second conveyor line 1B. With this arrangement, foreign matter 21F can be removed from a number of objects 21, and only glass fragments 21G are collected on second conveyor line 1B.

In the fifth embodiment, a reflection pattern detection system (22+25R) is arranged at the left side of FIG. 15. However, it can be arranged at the right side thereof. When this detection system (22+25R) is arranged as now presently illustrated in FIG. 15, distances L1 and L2 between the detection system (22+25R) and object 21 under inspection can be made substantially constant. However, when the detection system (22+25R) is arranged at the right side of FIG. 15, distances L1 and L2 vary, depending on the thicknesses of object 21, and the inspection apparatus could be operated erroneously.

In the embodiment of FIG. 15, objects 21 are conveyed one by one. If many objects 21 are irregularly conveyed as in the embodiment of FIG. 11, laser beam 23 is scanned using a rotary mirror (26), and parallel-arranged air jets (15) are appropriately driven so that foreign matter 21F, falling from line 1A to line 1B, can be removed.

The present invention is not limited to the first to fifth embodiments. For instance, in the above embodiments, the apparatus is used for distinguishing glass fragments 21G (translucent substances) from foreign matters 21F (nontranslucent substances, such as stones, ceramics, etc.). Of course, the present invention can be applied to an inspection apparatus for discriminating a material having a unique transmissivity upon radiation of coherent light, for example, laser beam 23. Further, the distance between patterns P1 and P2 or between P2 and P3 in FIG. 3D changes in accordance with the thickness of object 21, such as a glass plate. Accordingly, the flatness of plate-like object 21 can be inspected by measuring the distance between patterns P1 and P2 or between P2 and P3.

Figures 16A, 16B:
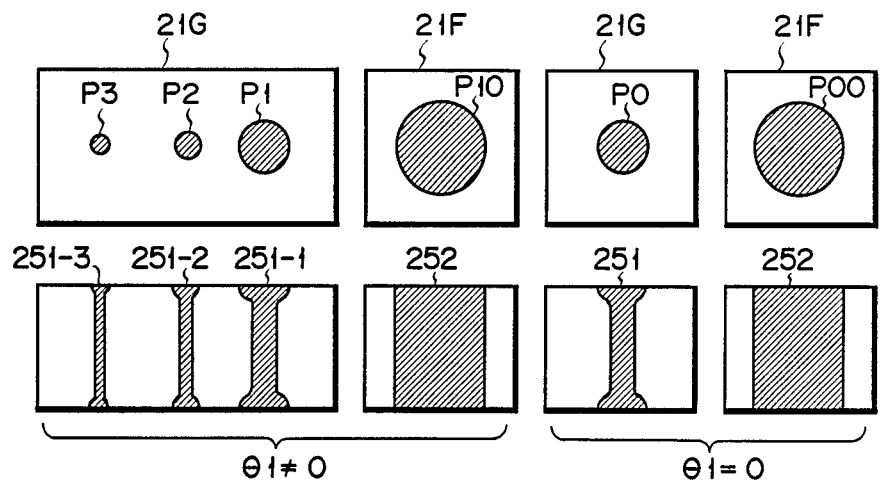
FIG. 16A illustrates patterns obtained for translucent and nontranslucent materials where laser beam incident angle $\theta_1 \neq 0$ (cf.
FIG. 16B illustrates patterns obtained for translucent and nontranslucent materials where laser beam incident angle $\theta_1 = 0$ (cf.

FIG. 16A illustrates patterns obtained for translucent material (glass) 21G and nontranslucent material (foreign matter such as stone) 21F where laser beam incident angle $\theta 1$ shown in FIG. 7 is not zero. FIG. 16A teaches that all areas P1–P3 of translucent material 21G are smaller than are a P10 of nontranslucent material 21F. The distance between P1 and P2 (or P2 and P3) becomes long as the thickness of translucent material 21G becomes large. Also, the area of P2 (or P3) becomes small as the thickness of translucent material 21G becomes large. Further, patterns 251-1 to 251-3, obtained by the laser beam scanning, becomes narrow as the thickness of translucent material 21G becomes large, and the width of each of these patterns (251-1 to 251-3) is narrower than the width of pattern 252 obtained for nontranslucent material 21F.

FIG. 16B illustrates patterns obtained for translucent and nontranslucent materials where laser beam incident angle $\theta 1$ shown in FIG. 7 is zero. FIG. 16B teaches that area P0 of translucent material 21G is smaller than area P00 of nontranslucent material 21F, and that the width of pattern 251, obtained by the laser beam scanning, is narrower than that of pattern 252 obtained for nontranslucent material 21F.

Figure 17:
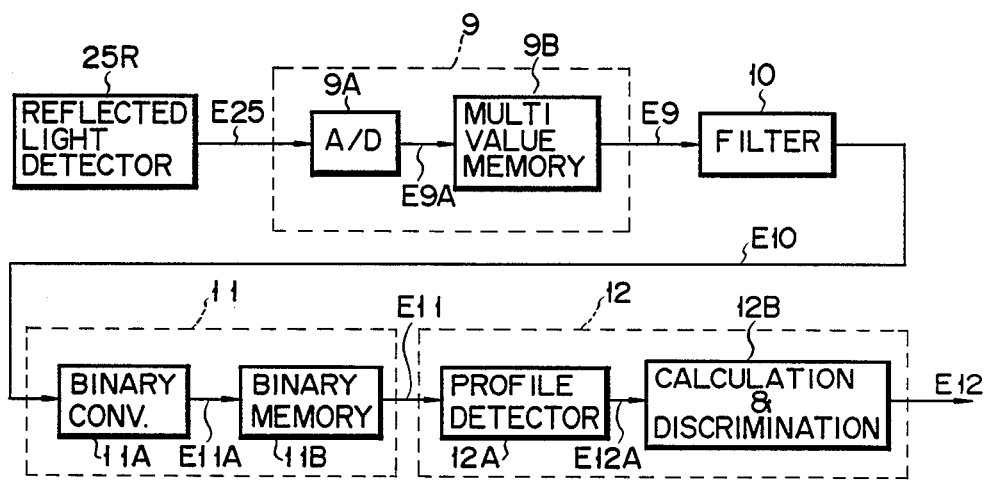
FIG. 17 shows details of circuit elements 9–12 in FIG. 7.
Figure 19A:
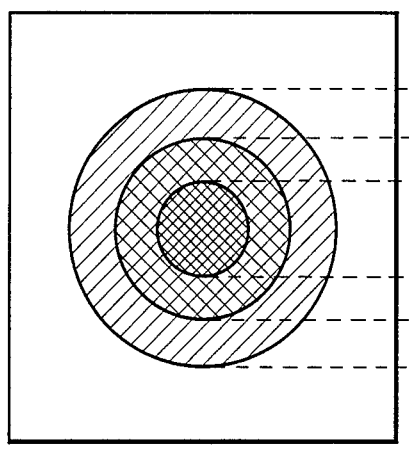
FIG. 19A shows an example of the reflected light pattern (P1–P3, P10, etc.) having three different intensities.
Figure 19B:
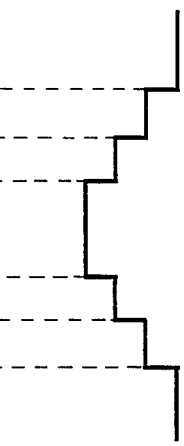
FIG. 19B shows a profile of the pattern shown in FIG. 19A, which is obtained from a profile detector (12A) in FIG. 17.
Figure 20A:
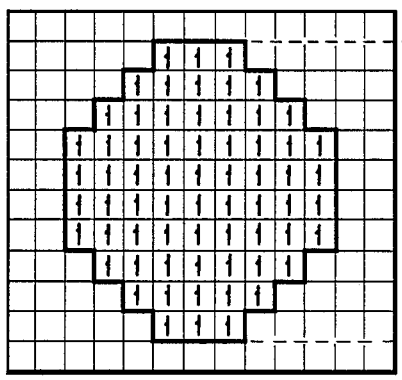
FIG. 20A shows an example of the binary-converted signals obtained for a low intensity pattern image.
Figure 20B:
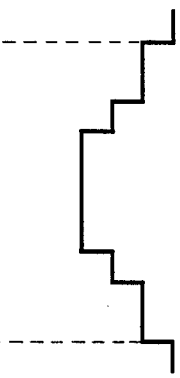
FIG. 20B shows a profile of the low intensity pattern image corresponding to FIG. 20A.
Figure 21A:
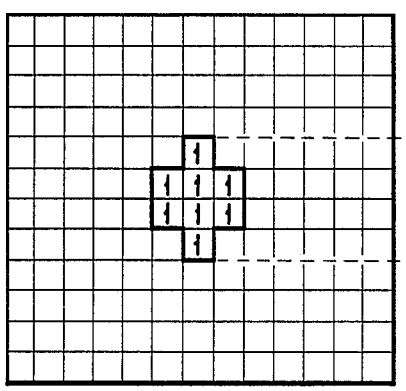
FIG. 21A shows an example of the binary-converted signals obtained for a high intensity pattern image.
Figure 21B:
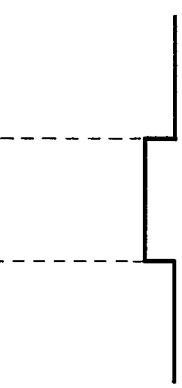
FIG. 21B shows a profile of the high intensity pattern image corresponding to FIG. 21A.

FIG. 17 shows details of circuit elements 9–12 in FIG. 7. FIGS. 18A–18E exemplify the contents of signals obtained from the circuit elements in FIG. 17. FIG. 19A shows an example of the reflected light pattern (P1–P3, P10, etc.) having three different intensities. FIG. 19B shows a profile of the pattern shown in FIG. 19A, which is obtained from profile detector 12A in FIG. 17. FIG. 20A shows an example of the memory arrangement of binary-converted signal E11 obtained for a low intensity pattern image. FIG. 20B shows a profile of the low intensity pattern image corresponding to FIG. 20A. FIG. 21A shows an example of the memory arrangement of binary-converted signal E11 obtained for a high intensity pattern image. FIG. 21B shows a profile of the high intensity pattern image corresponding to FIG. 21A.

Analog signal E25 (FIG. 18B), containing pattern information (P1) as shown in FIG. 18A, is supplied from reflected light detector 25R to A/D converter 9A. A/D converter 9A provides multi-value digital signal E9A which represents the intensity of signal E25. Such digital signal E9A is stored in multi value memory 9B.

Digital output E9 (FIG. 18D) from memory 9B, corresponding to signal E9A, is filtered by filter 10 so as to eliminate noise from output E9. Then, filtered signal E10 is converted, via binary converter 11A, into binary signal E11A. Binary signal E11A is stored in binary memory 11B.

Binary output E11 (FIG. 18E) from memory 11B is supplied to profile detector 12A. Detector 12A detects, based on data "1" of output E11, the profile (FIGS. 18C, 19B–21B) of the detected image pattern. The area of the profile is detected in calculator/discriminator 12B, by calculating the total number of the data "1" encircled within the profile of output E11. When the value of the calculated area exceeds a predetermined value, calculator/discriminator 12B discriminates that the object (21), providing signal E25, is foreign matter 21F, and generates foreign matter removal instruction E12.

Figure 24:
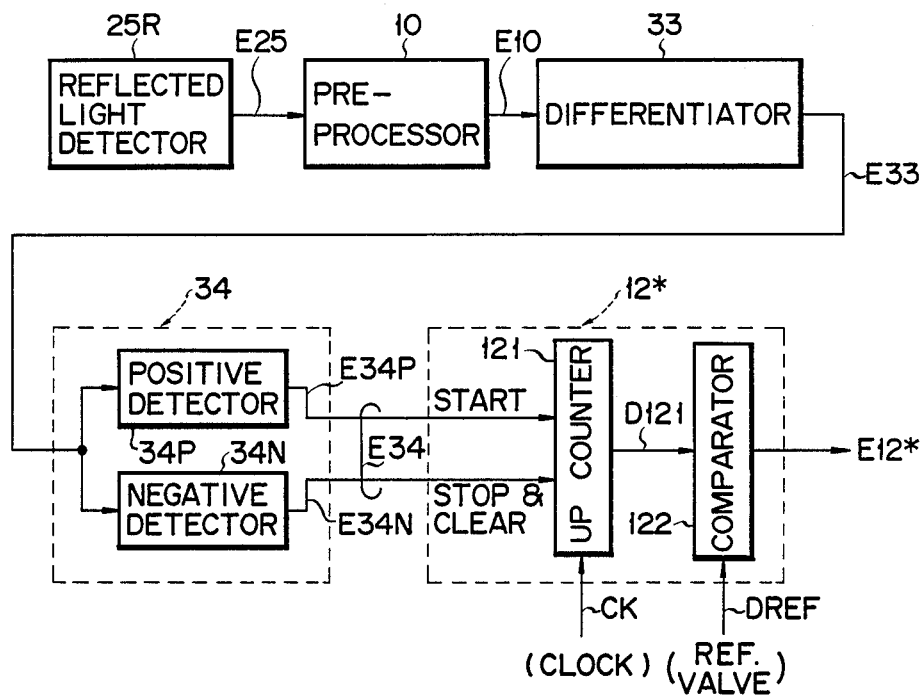
FIG. 24 shows an example of circuit elements 34 and 12* in FIG. 8, which is responsive to a discrimination value (DREF) shown in FIG. 23F.

FIGS. 22A–22I are timing charts explaining how a translucent pattern (251) is discriminated by discriminator 12* in FIG. 8. FIGS. 23A–23I are timing charts explaining how a nontranslucent pattern (252) is discriminated by discriminator 12* in FIG. 8. FIG. 24 shows an example of circuit elements 34 and 12* in FIG. 8, which is responsive to a discrimination value (DREF) shown in FIGS. 22F and 23F.

The circuit of FIG. 24 responds to sensing area SA1 or SA3 shown in FIGS. 22A and 23A. Differentiated output signal E33 (FIGS. 22C and 23C) from differentiator 33 is supplied to positive detector 34P and negative detector 34N. Positive detector 34P responds only to the positive component of signal E33 and outputs positive pulse E34P (FIGS. 22D and 23D). Negative detector 34N responds only to the negative component of signal E33 and outputs negative pulse E34N (FIGS. 22E and 23E). Pulse E34P is supplied to up-counter 121, so that counter 121 starts up-counting of clock pulse CK. Pulse E34N is also supplied to counter 121, so that counter 121 stops the counting of clock pulse CK, and it is then cleared. Count value D121 (FIGS. 22F and 23F) of counter 121 is latched by a latch (not shown) contained in counter 121, before it is cleared.

Count value D121 is compared with predetermined reference value DREF at comparator 122. When D121<DREF, discriminator 12* discriminates that the object (21) under inspection is, for example, glass, and no removal instruction 12* is generated (FIG. 22G). If D121≧DREF, discriminator 12* discriminates that the object (21) under inspection is, for example, stone, and removal instruction 12* is generated (FIG. 23G).

Figure 25:
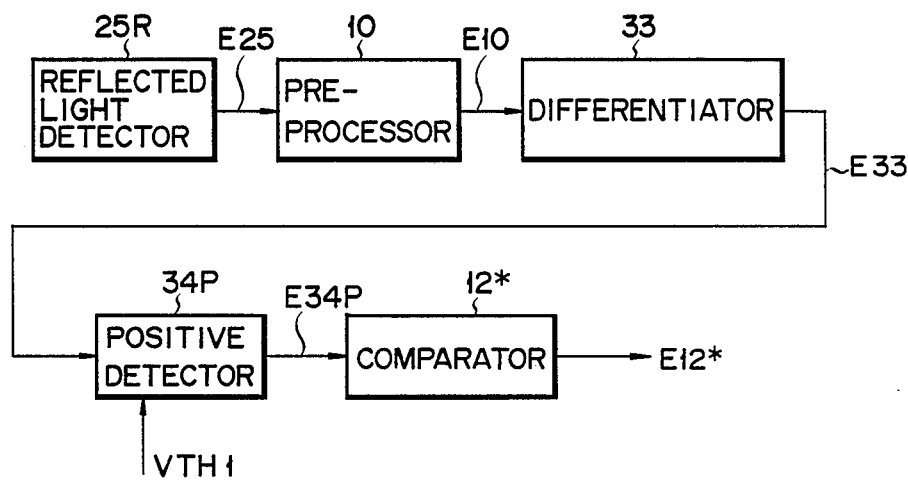
FIG. 25 shows an example of circuit elements 34 and 12* in FIG. 8, which is responsive to a discrimination threshold level (VTH1) shown in FIG. 22B.

FIG. 25 shows an example of circuit elements 34 and 12* in FIG. 8, which is responsive to detection area SA2 shown in FIGS. 22A and 23A and to discrimination threshold level VTH1 shown in FIGS. 22B and 23B. Differentiated output signal E33 (FIGS. 22C and 23C) from differentiator 33 is supplied to positive detector 34P. Positive detector 34P responds only to the positive component of signal E33 having a signal level higher than VTH1. When E33<VTH1, detector 34P provides no pulse. However, if E33≧VTH1, detector 34P outputs positive pulse E34P. Then, comparator 12* generates removal instruction E12* in response to E34P (FIG. 23G).

Figure 26:
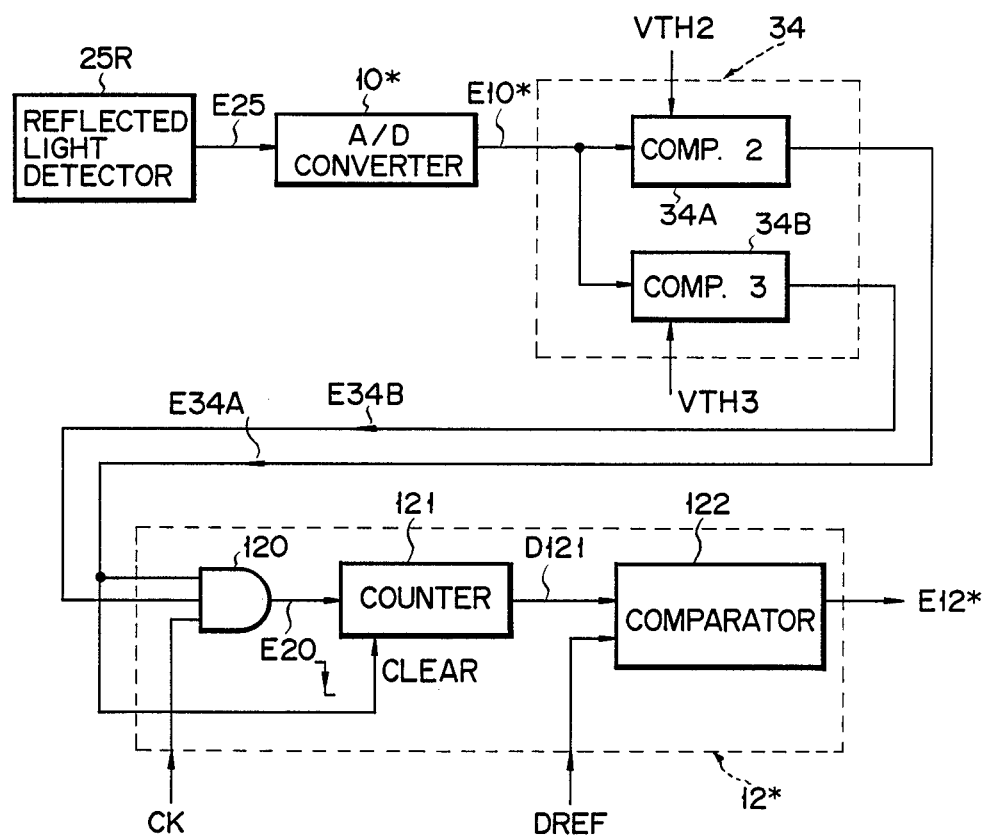
FIG. 26 shows an example of circuit elements 34 and 12* in FIG. 8, which is responsive to two different discrimination threshold levels (VTH2 and VTH3) shown in FIG. 22B.

FIG. 26 shows an example of circuit elements 34 and 12* in FIG. 8, which is responsive to detection area SA2 shown in FIGS. 22A and 23A and to discrimination threshold levels VTH2 and VTH3 shown in FIGS. 22B and 23B. Analog video signal E25 from reflected light detector 25R is analog-to-digital converted via A/D converter 10*. A/D converted digital signal E10* from converter 10* is supplied to digital comparators 34A and 34B. Comparator 34A compares the digital value of E10* with that of VTH2, and comparator 34B compares the digital value of E10* with that of VTH3.

When an object (21) exists in the inspection area, the relation E10*>VTH3 is always obtained, so that comparator 34B always generates pulse E34B with logic "1" level (FIGS. 22H and 23H). When the object is translucent material 21G, comparator 34A generates pulse E34A with logic "1" level, only if E10*>VTH2 (FIGS. 22B and 22I). On the other hand, when the object is nontranslucent material 21F, comparator 34A generates pulse E34A with logic "1" level, since E110*>VTH2 (FIGS. 23B and 23I).

Pulses 34A and 34B are input to AND gate 120. AND gate 120 also receives clock pulse CK. When both pulse 34A and 34B are logic "1", pulse CK passes AND gate 120 and is supplied to counter 121. Counter 121 counts pulse CK until it is cleared. Counter 121 is cleared by the falling edge of pulse E34A. Before cleared, a latch (not shown) of counter 121 latches count value D121 of CK. This count value indicates the pulse width of E34A, and indicates whether or not the object (21) is translucent.

Count value D121 is compared with predetermined reference value DREF at comparator 122. When D121<DREF, discriminator 12* discriminates that the object (21) under inspection is translucent, and no removal instruction 12* is generated (FIG. 22G). If D121≧DREF, discriminator 12* discriminates that the object (21) under inspection is nontranslucent, and removal instruction 12* is generated (FIG. 23G).

According to the present invention as described above, coherent light is radiated onto an object to be inspected, reflected beams from the object are detected, and a transmissivity of the object with respect to the light is inspected based on the irregular reflection components of the detected reflected beams. Therefore, a transmissivity inspection apparatus can automatically and highly reliably detect a nontranslucent substance mixed with translucent substances.

While the invention has been described in connection with what is presently considered to be the most practical and preferred embodiment, it is understood that the invention is not to be limited to the disclosed embodiment but, on the contrary, is intended to cover various modifications and equivalent arrangements included within the scope of the appended claims, which scope is to be accorded the broadest interpretation so as to encompass all such modifications and equivalent structures.

What is claimed is:

1. A transmissivity inspection apparatus, comprising:
   light source means for supplying coherent light to an object to be inspected;
   reflection detection means for detecting irregular reflection components of the coherent light emitted from said object; and
   transmissivity inspection means, coupled to said reflection detection means, for inspecting a transmissivity of said object with respect to said coherent light based on a specific pattern of said irregular reflection components, and generating an inspection signal indicating that said object includes a material having a transmissivity lower than a predetermined transmissivity.

2. An apparatus according to claim 1, wherein said light source means supplies coherent light beam to said object so that a beam spot is formed on said object under inspection, and
   when said object under inspection includes a substantially nontransparent material for said coherent light, said specific pattern has an area larger than an area of another specific pattern obtained for a substantially transparent material.

3. An apparatus according to claim 2, wherein said transmissivity inspection means includes:
   preprocessor means, coupled to said reflection detection means, for converting said irregular reflection components into electrical signal;
   binary converter means, coupled to said preprocessor means, for converting said electrical signal into binary signal indicating the area of said specific pattern; and
   discriminator means, coupled to said binary converter means, for generating said inspection signal when said binary signal contains information that the area of said specific pattern is larger than a predetermined value.

4. An apparatus according to claim 1, wherein said light source means supplies coherent light beam to said object so that a beam spot is formed on said object under inspection, and
   when said object under inspection includes a substantially nontransparent material for said coherent light, the number of said specific pattern is smaller than that of other specific patterns obtained for a substantially transparent material.

5. An apparatus according to claim 1, wherein said light source means supplies coherent light beam to an edge portion of said object so that a beam spot of said coherent light beam is formed at the edge portion, and
   when said object under inspection includes a substantially transparent material for said coherent light beam, said specific pattern has a portion at which a configuration of the pattern changes abruptly.

6. An apparatus according to claim 1, wherein said light source means includes means for converting said coherent light into scanning coherent light beam to be scanned over said object, and when said object under inspection includes a substantially transparent material for said coherent light beam, said specific pattern has portions at which a configuration of said specific pattern changes abruptly.

7. An apparatus according to claim 1, wherein said light source means includes means for converting said coherent light into scanning coherent light beam to be scanned over said object, and when said object under inspection includes a substantially transparent material for said coherent light beam, said specific pattern has a narrowed portion having a given length formed between two portions at which a configuration of said specific pattern changes abruptly.

8. An apparatus according to claim 7, wherein said transmissivity inspection means includes:

means for detecting the narrowed portion of said specific pattern.

9. An apparatus according to claim 7, wherein said transmissivity inspection means includes:

preprocessor means, coupled to said reflection detection means, for converting said irregular reflection components into electrical signal;

differentiator means, coupled to said preprocessor means, for differentiating said electrical signal to provide a differentiated signal; and signal detector means, coupled to said differentiator means, for detecting whether said differentiated signal contains a specific pair of positive and negative waveforms which indicates that said object includes a material substantially transparent with respect to said coherent light.

10. An apparatus according to claim 1, wherein said transmissivity inspection means detects portions exhibiting a specific transmissivity being different from the transmissivity of other portion of said object, in accordance with an irregular reflection pattern of the coherent light reflected from said object under inspection.

11. An apparatus according to any one of claims 1 to 10, further comprising:

means for removing said low transmissivity material from a number of the inspected objects when said transmissivity inspection means generates said inspection signal.

* * * * *